United States Patent
Lesso

(10) Patent No.: US 12,340,820 B2
(45) Date of Patent: Jun. 24, 2025

(54) HEALTH-RELATED INFORMATION GENERATION AND STORAGE

(71) Applicant: Cirrus Logic International Semiconductor Ltd., Edinburgh (GB)

(72) Inventor: John Paul Lesso, Edinburgh (GB)

(73) Assignee: Cirrus Logic Inc., Austin, TX (US)

( * ) Notice: Subject to any disclaimer, the term of this patent is extended or adjusted under 35 U.S.C. 154(b) by 112 days.

(21) Appl. No.: 18/359,577

(22) Filed: Jul. 26, 2023

(65) Prior Publication Data

US 2023/0377602 A1    Nov. 23, 2023

Related U.S. Application Data

(63) Continuation of application No. 16/404,116, filed on May 6, 2019, now Pat. No. 11,749,298.

(60) Provisional application No. 62/668,517, filed on May 8, 2018.

(51) Int. Cl.
*G10L 25/66* (2013.01)
*A61B 7/00* (2006.01)
*G16H 10/00* (2018.01)

(52) U.S. Cl.
CPC .............. *G10L 25/66* (2013.01); *A61B 7/003* (2013.01); *G16H 10/00* (2018.01)

(58) Field of Classification Search
CPC .......... G10L 25/66; G16H 10/00; A61B 7/003
USPC .......................................................... 702/19
See application file for complete search history.

(56) References Cited

U.S. PATENT DOCUMENTS

| 5,671,733 | A  | * | 9/1997  | Raviv        | A61B 7/003  |
|           |    |   |         |              | 600/587     |
| 10,004,452| B2 | * | 6/2018  | Kazem-Moussavi | A61B 5/742 |
| 12,148,014| B1 | * | 11/2024 | Bini         | G16H 20/13  |
| 2002/0171551 | A1 | * | 11/2002 | Eshelman  | G08B 21/0423 |
|           |    |   |         |              | 340/573.1   |

(Continued)

FOREIGN PATENT DOCUMENTS

CN     112786133 A    5/2021
CN     113948109 A    1/2022

(Continued)

OTHER PUBLICATIONS

Partial International Search Report and Provisional Opinion of the International Searching Authority, International Application No. PCT/GB2019/051248, mailed Aug. 22, 2019.

(Continued)

*Primary Examiner* — Omar Flores Sanchez
(74) *Attorney, Agent, or Firm* — Jackson Walker L.L.P.

(57) ABSTRACT

A detected sound signal may comprise speech or non-verbal sounds, and many non-verbal sounds contain health information. If the speech, or a non-verbal sound containing health information, was produced by an enrolled user, data relating to the sound can be stored in a storage element. A system also comprises a data modification block, for obfuscating received data to provide an obfuscated version of the stored data. The system then has a first access mechanism, for controlling access to the stored data such that only an authorised user can obtain access to said stored data, and a second access mechanism, for controlling access to said stored data such that the second access mechanism only provides access to the obfuscated version of the stored data.

10 Claims, 8 Drawing Sheets

(56) References Cited

U.S. PATENT DOCUMENTS

| | | | | |
|---|---|---|---|---|
| 2012/0130645 | A1* | 5/2012 | Garudadri | G16H 40/67 |
| | | | | 702/19 |
| 2014/0095577 | A1* | 4/2014 | Root | A61B 5/14532 |
| | | | | 709/217 |
| 2015/0297169 | A1* | 10/2015 | Copt | A61B 5/7257 |
| | | | | 600/586 |
| 2019/0038216 | A1* | 2/2019 | Ser | G16H 50/20 |
| 2020/0035261 | A1 | 1/2020 | Mitchell et al. | |
| 2020/0388380 | A1 | 12/2020 | Romanychev et al. | |
| 2021/0027893 | A1* | 1/2021 | Nematihosseinabadi | |
| | | | | G16H 10/60 |
| 2021/0319804 | A1 | 10/2021 | Whitehill et al. | |
| 2021/0390959 | A1* | 12/2021 | Jain | A61B 5/7267 |
| 2022/0096002 | A1* | 3/2022 | Ayers | A61B 5/6817 |
| 2022/0133156 | A1* | 5/2022 | Hartley | A61B 5/7264 |
| | | | | 600/301 |
| 2022/0151582 | A1* | 5/2022 | Peters | A61B 5/7267 |

FOREIGN PATENT DOCUMENTS

| | | |
|---|---|---|
| EP | 2575064 A1 | 4/2013 |
| EP | 3671751 A1 | 6/2020 |
| WO | 2007121570 A1 | 11/2007 |
| WO | 2017210661 A1 | 12/2017 |

OTHER PUBLICATIONS

Combined Search and Examination Report under Sections 17 and 18(3), UKIPO, Application No. GB2210385.7, mailed Aug. 16, 2022.

Combined Search and Examination Report under Sections 17 and 18(3), UKIPO, Application No. GB2210386.5, mailed Aug. 16, 2022.

* cited by examiner

HEALTH-RELATED INFORMATION GENERATION AND STORAGE

The present application is a continuation of U.S. Non-provisional patent application Ser. No. 16/404,116, filed May 6, 2019, which claims priority to U.S. Provisional Patent Application Ser. No. 62/668,517, filed May 8, 2018, which is incorporated by reference herein in its entirety.

FIELD OF THE INVENTION

This relates to the generation and storage of medical information.

BACKGROUND

It is known that medically-relevant information can be obtained from a person's speech, and also from non-speech sounds that they generate, such as coughs, sneezes and the like.

Smartphones are of course provided with microphones, and, as they are commonly carried, they have the potential to detect the speech, and the non-speech sounds, produced by their owner. However, in order to be medically relevant, it is necessary to be sure that the sounds that are detected were actually produced by the person whose health is being analysed. Further, it is necessary to be sure that any health-related information that is generated within the device is stored in a suitably secure way.

SUMMARY

According to a first aspect of the invention, there is provided a method of obtaining information relevant to a user's health, the method comprising: detecting a sound; determining whether the detected sound comprises a non-verbal sound containing health information; if it is determined that the detected sound comprises a non-verbal sound containing health information, determining whether the non-verbal sound was produced by the user; and if it is determined that the non-verbal sound was produced by the user, storing data relating to said non-verbal sound.

According to a second aspect of the invention, there is provided a method of monitoring an enrolled user's health, comprising: receiving an audio signal representing speech; performing a speaker recognition process on the received audio signal to identify a speaker; if it is determined that the identified speaker is an enrolled user, obtaining health marker features from the speech represented by the audio signal; and storing the obtained health marker features together with data indicating the identified speaker in a secure storage element.

According to a third aspect of the invention, there is provided a data storage system for health-related data, comprising: a storage element, for storing input data, wherein input data is stored after determination that it relates to an enrolled user; a data modification block, for receiving said input data, and for obfuscating said received input data to provide an obfuscated version of said stored data; a first access mechanism, for controlling access to said stored data such that only an authorised user can obtain access to said stored data; and a second access mechanism, for controlling access to said stored data such said second access mechanism only provides access to the obfuscated version of the stored data.

BRIEF DESCRIPTION OF DRAWINGS

For a better understanding of the invention, and to show more clearly how it may be carried into effect, reference will now be made, by way of example only, to the accompanying drawings in which.

DETAILED DESCRIPTION

The description below sets forth example embodiments according to this disclosure. Further example embodiments and implementations will be apparent to those having ordinary skill in the art. Further, those having ordinary skill in the art will recognize that various equivalent techniques may be applied in lieu of, or in conjunction with, the embodiments discussed below, and all such equivalents should be deemed as being encompassed by the present disclosure.

For clarity, it will be noted here that this description refers to speaker recognition and to speech recognition, which are intended to have different meanings. Speaker recognition refers to a technique that provides information about the identity of a person speaking. For example, speaker recognition may determine the identity of a speaker, from amongst a group of previously registered individuals (speaker identification), or may provide information indicating whether a speaker is or is not a particular individual (speaker verification), for example for the purposes of authentication. Speech recognition refers to a technique for determining the content and/or the meaning of what is spoken, rather than recognising the person speaking.

Figure 1:
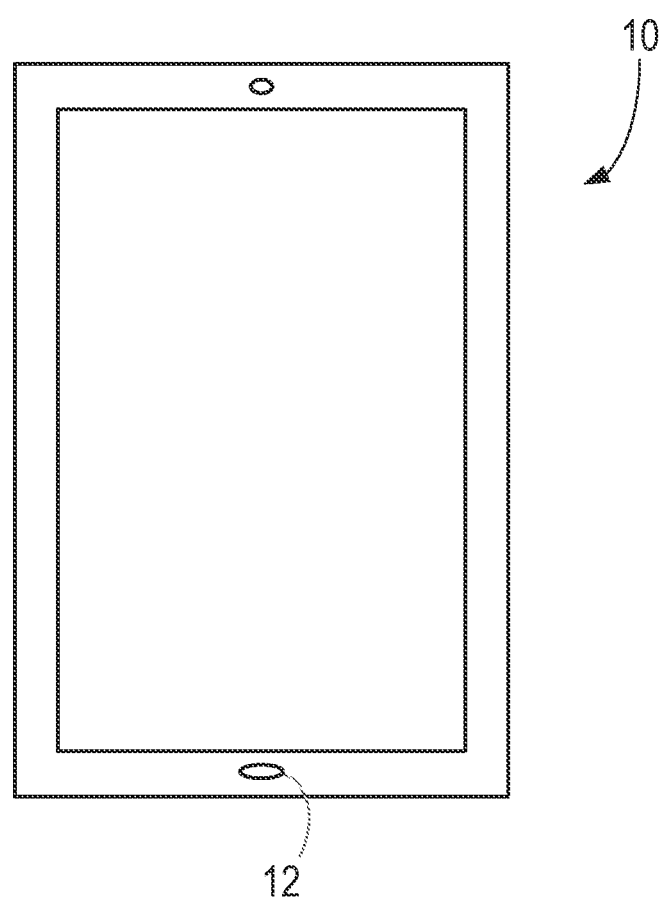
FIG. 1 shows a smartphone.

FIG. 1 illustrates a smartphone 10, having a microphone 12 for detecting ambient sounds. The smartphone 10 is just one example of an electronic device in which the systems described herein can be implemented, and the methods described herein can be performed. Other examples of electronic devices in which the systems described herein can be implemented, and the methods described herein can be performed, are tablet or laptop computers, games consoles, home control systems, home entertainment systems, in-vehicle entertainment systems, and domestic appliances.

Figure 2:
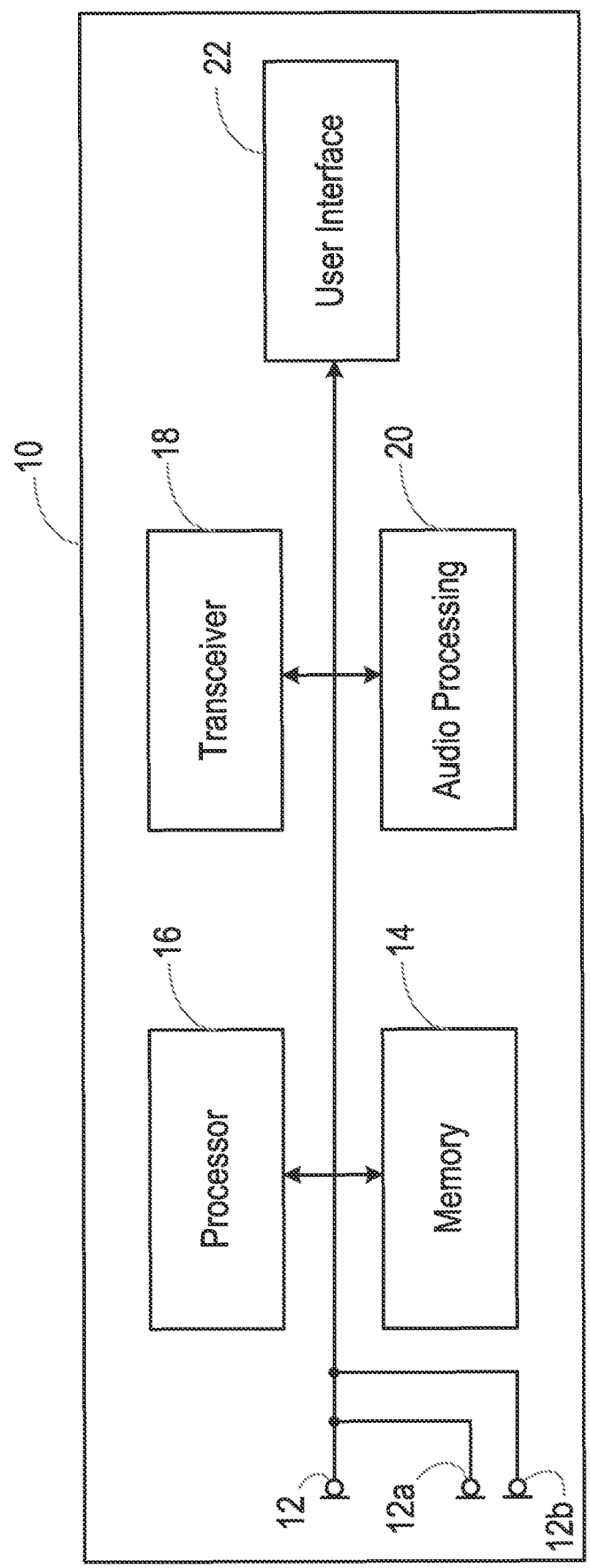
FIG. 2 is a schematic diagram of the smartphone.

FIG. 2 is a schematic diagram, illustrating the form of the smartphone 10 or other electronic device.

Specifically, FIG. 2 shows various interconnected components of the smartphone 10. It will be appreciated that the smartphone 10 will in practice contain many other components, but the following description is sufficient for an understanding of the present invention.

Thus, FIG. 2 shows the microphone 12 mentioned above. In certain embodiments, the smartphone 10 is provided with multiple microphones 12, 12a, 12b, etc.

FIG. 2 also shows a memory 14, which may in practice be provided as a single component or as multiple components. The memory 14 is provided for storing data and program instructions.

FIG. 2 also shows a processor 16, which again may in practice be provided as a single component or as multiple components. For example, one component of the processor 16 may be an applications processor of the smartphone 10.

FIG. 2 also shows a transceiver 18, which is provided for allowing the smartphone 10 to communicate with external networks. For example, the transceiver 18 may include circuitry for establishing an internet connection either over a WiFi local area network or over a cellular network.

FIG. 2 also shows audio processing circuitry 20, for performing operations on the audio signals detected by the microphone 12 as required. For example, the audio processing circuitry 20 may filter the audio signals or perform other signal processing operations.

FIG. 2 also shows a user interface 22, for providing information to a user and/or receiving inputs from a user. For example, the user interface 22 may comprise a touchscreen display.

In some embodiments, the smartphone 10 is provided with speaker recognition functionality, and with control functionality. Thus, the smartphone 10 is able to perform various functions in response to spoken commands from an enrolled user. The speaker recognition functionality is able to distinguish between spoken commands from an enrolled user, and the same commands when spoken by a different person. Thus, certain embodiments of the invention relate to operation of a smartphone or another portable electronic device with some sort of voice operability, for example a tablet or laptop computer, a games console, a home control system, a home entertainment system, an in-vehicle entertainment system, a domestic appliance, or the like, in which the speaker recognition functionality is performed in the device that is intended to carry out the spoken command. Certain other embodiments relate to systems in which the speaker recognition functionality is performed on a smartphone or other device, which then transmits the commands to a separate device if the speaker recognition functionality is able to confirm that the speaker was an enrolled user.

In some embodiments, while speaker recognition functionality is performed on the smartphone 10 or other device that is located close to the user, the spoken commands are transmitted using the transceiver 18 to a remote speech recognition system, which determines the meaning of the spoken commands. For example, the speech recognition system may be located on one or more remote server in a cloud computing environment. Signals based on the meaning of the spoken commands are then returned to the smartphone 10 or other local device.

In other embodiments, a first part of the speaker recognition functionality is performed on the smartphone 10 or other device that is located close to the user. Then, as described in more detail below, a signal may be transmitted using the transceiver 18 to a remote system, which performs a second part of the speaker recognition functionality.

It is apparent that a smartphone can in theory be used to provide potentially medically relevant information about a user, based on their speech, and based on the non-speech sounds that they produce. However, work that has been carried out in these areas has typically been carried out in unnatural situations, for example where a particular user is asked to speak at specific times, or where it can be assumed that the sounds that are detected were produced by that one user. Methods that are described below allow the information to be generated in natural situations, on a more continuous basis.

Embodiments described herein relate to non-speech sounds produced by a user, and to the user's speech.

Figure 3:
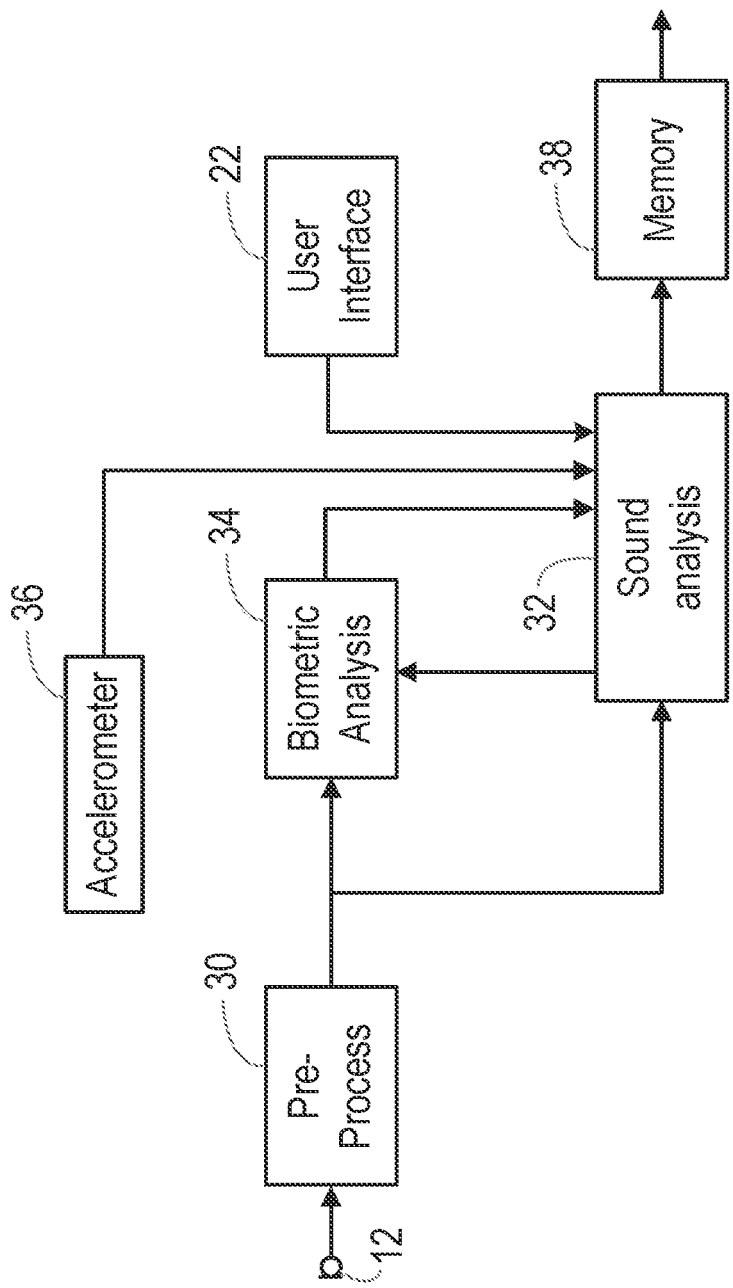
FIG. 3 is a block diagram, illustrating a first processing system.
Figure 4:
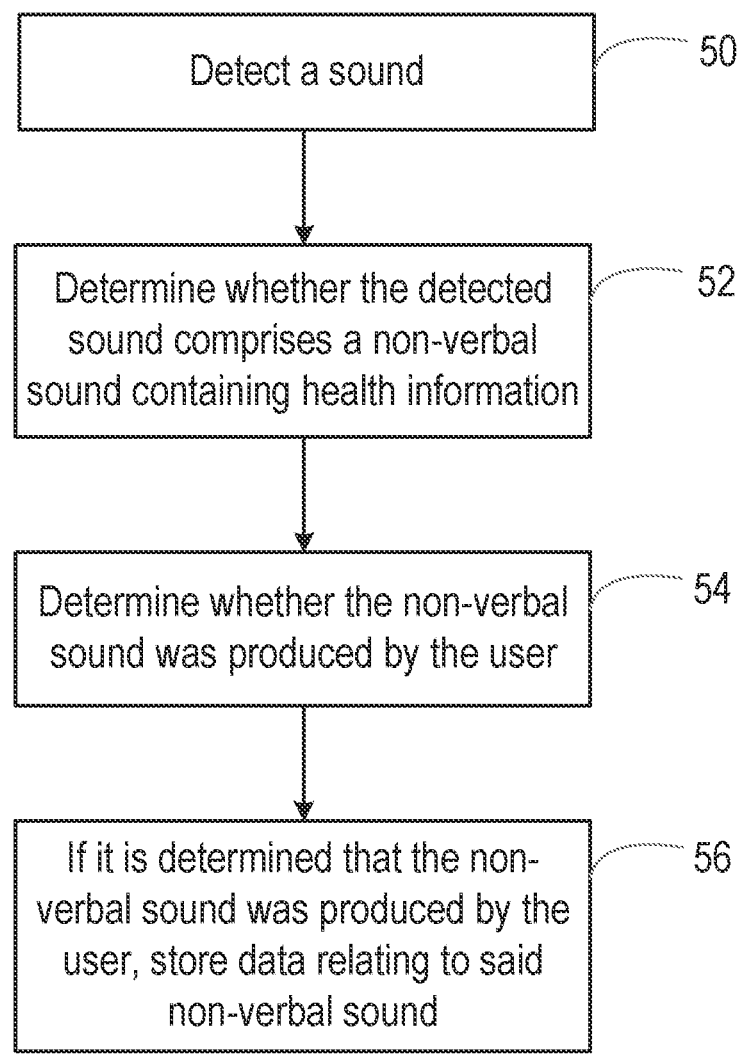
FIG. 4 is a flow chart, illustrating a first method.

FIG. 3 is a schematic block diagram of a system that can be implemented on the smartphone 10, and FIG. 4 is a flow chart illustrating a method performed by the system, for obtaining information relevant to a user's health.

FIG. 3 shows one of the microphones 12 on the smartphone 10. As shown at step 50 of FIG. 4, the microphone 10 will detect sounds in the vicinity of the smartphone 10. Although only one microphone 10 is shown in FIG. 3, the sounds detected by multiple microphones can be used in the method.

A signal generated by the microphone 10 is passed to a pre-processing block 30. For example, if the signal generated by the microphone 10 is an analog signal, the pre-processing block 30 may perform analog-to-digital conversion. The signal may also be divided into frames, for example of 20 ms duration, such that each frame can be considered separately.

The pre-processed signal is passed to a sound analysis block 32, which determines in step 52 of the process shown in FIG. 4 whether the detected sound comprises a non-verbal sound containing health information.

For example, in some embodiments, the non-verbal sound is a cough; in some embodiments, the non-verbal sound is a sneeze; and, in some embodiments, the non-verbal sound is an audible breathing sound. In some embodiments, the sound analysis block 32 is configured to detect multiple non-verbal sounds.

Each of these sounds contains health information. Thus, the fact that a user has coughed can be used to deduce information about a medical condition of the user. The sound analysis block may also extract additional information about the type of cough. For example, the sound analysis block 32 may be able to distinguish between a productive cough, a non-productive cough, and a whooping cough. Similarly, the fact that a user has sneezed can be used to deduce information about a medical condition of the user. Again, the fact that the user's breathing is audible can also be used to deduce information about a medical condition of the user. The sound analysis block may also extract additional information about the sound of the breathing.

Thus, the sound analysis block 32 may be provided with models that represent the specific non-verbal sounds that it is concerned with, such as coughs, sneezes, snoring or other audible breathing sounds, passing wind (either by belching or flatulence), or hiccups. The pre-processed signal may then be compared in the sound analysis block 32 with these models, in order to determine whether one of these sounds has been detected.

In addition, the sound analysis block 32 may generate time stamp data to be associated with the information about the non-verbal sound, relating to a time at which the sound was produced. In addition, or alternatively, the sound analysis block 32 may generate data relating to a duration of the sound. In addition, or alternatively, the sound analysis block 32 may keep a count of a number of said non-verbal sounds produced.

In addition, the sound analysis block 32 may generate data relating to audible features of the sound. In addition, or alternatively, the sound analysis block 32 may perform an analysis of the non-verbal sound, and generate data relating to a result of said analysis.

In step 54 of the process shown in FIG. 4, if it is determined that the detected sound comprises a non-verbal sound containing health information, it is determined whether the non-verbal sound was produced by the user.

The process of determining whether the non-verbal sound was produced by the user may take one or more of several different forms.

For example, the pre-processed signal output by the pre-processing block 30 may be passed to a biometric analysis block 34, and the step of determining whether the non-verbal sound was produced by the user may comprise performing a biometric process on the detected sound.

More specifically, in one example, it has been recognised that the sound made by a person when coughing can be used as a biometric identifier for that person. Thus, when the non-verbal sound is a cough, performing the biometric process may comprise comparing the detected sound with coughs produced previously by the user. One possibility is to ask the user to perform an enrolment process by deliberately coughing, because it has been suggested that such a forced cough has many of the characteristics of an unforced cough. The features of that user's cough can then be extracted in a conventional way and stored, and used as a model. For example, the features that are extracted may include features representing the input audio that can also be used for performing speaker recognition. For example, the features that are extracted could include Mel Frequency Cepstral Coefficients (MFCCs).

The enrolment process may take place over a prolonged period, for example several days, so that it can use several examples of the enrolling user producing the sound. The system may ask the user to produce the sound on one or more occasions. Alternatively, or additionally, when the system detects the relevant sound (for example a cough or a sneeze), it may prompt the user to confirm that they made that sound. The multiple sounds produced by the user may then be used for the purposes of enrolment.

Also the enrolment may include an enrichment stage, wherein, even after enrolment, subsequent sounds are analysed and used to improve the model for that specific user. This assists in allowing the system to identify variability between the coughs (or other sounds) of a specific user, as well as the variability between that user and others.

Then, when a user has been enrolled in the system, and a model has been created, comparing the detected sound with corresponding non-verbal sounds produced previously by the user may comprise extracting the same features from the part of a received audio signal that represents a cough (or other sound), and comparing the extracted features of the cough against the model produced during enrolment. If the degree of similarity is sufficient, it may be determined that the cough was produced by the enrolled user. Whether or not an initial enrolment is performed, coughs or other non-verbal sounds that are detected by the sound analysis block 32 may be compared with corresponding non-verbal sounds that are recognised as having been produced previously by the user.

In another example, the step of determining whether the non-verbal sound was produced by the user may comprise requesting the user to confirm whether they produced said non-verbal sound.

For example, if the sound analysis block 32 determines that it has detected a sneeze, it may send a signal to the user interface 22 of the smartphone, for example causing a touchscreen to display a message:

"Was it you that just sneezed? Press button YES or NO".

The step of determining whether the non-verbal sound was produced by the user may then comprise recording the sneeze as having been produced by the user only if a "YES" button that is displayed on the screen is pressed.

In another example, the step of determining whether the non-verbal sound was produced by the user may comprise receiving information relating to movement of a device being worn or carried by the user.

For example, if a person sneezes, this usually causes their head to move slightly. The sound analysis block may therefore receive signals that are generated by an accelerometer 36 that is provided in an earphone being worn by the user. The earphone may have a wired or wireless connection to the smartphone 10. If signals that are characteristic of a head movement that is typical of a person sneezing are received at the same time as the sound of a sneeze, it can be determined that it is the user of the smartphone 10 who sneezed.

In step 56 of the process shown in FIG. 4, if it is determined that the non-verbal sound was produced by the user, the data relating to said non-verbal sound is stored. For example, as shown in FIG. 3, the data may be stored in a memory 38. When required, the audio signal containing the sound may also be stored in the memory 38. As described in more detail below, the memory 38 may be a secure storage device, which may be integrated with the processor that performs the analysis and classification in a System on a Chip, or may be securely connected to the processor.

Thus, this method and system have the advantage that information about non-verbal sounds can be stored. The information that is stored is clinically relevant. For example, in the case of a person suspected of a chronic chest illness, accurate information can be obtained about the number of times that the person coughs, and other relevant audible features of the coughs can also be obtained. For a person with a condition such as obstructive sleep apnea, information about the duration and frequency of audible breathing effects can be obtained.

In addition, the method and system are able to distinguish the coughs and sneezes of the person using the device from other coughs and sneezes that might be detected by the microphone. This avoids a situation where, for example, a count of the number of times that a user coughs is confounded by detecting other people coughing.

Figure 5:
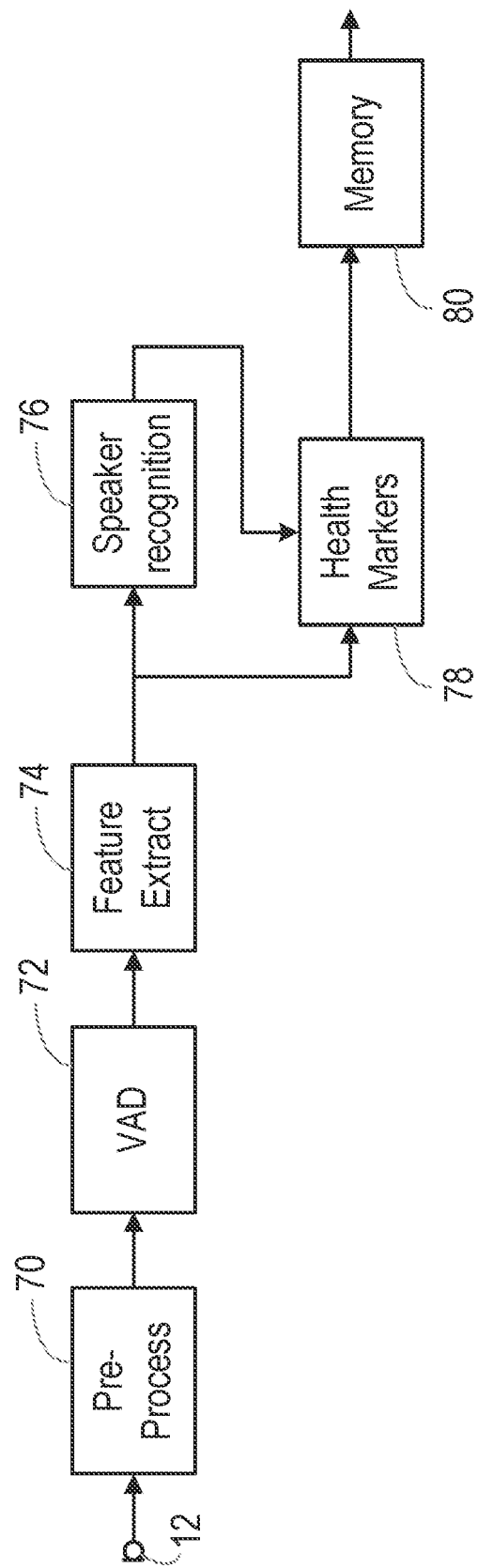
FIG. 5 is a block diagram, illustrating a second processing system.
Figure 6:
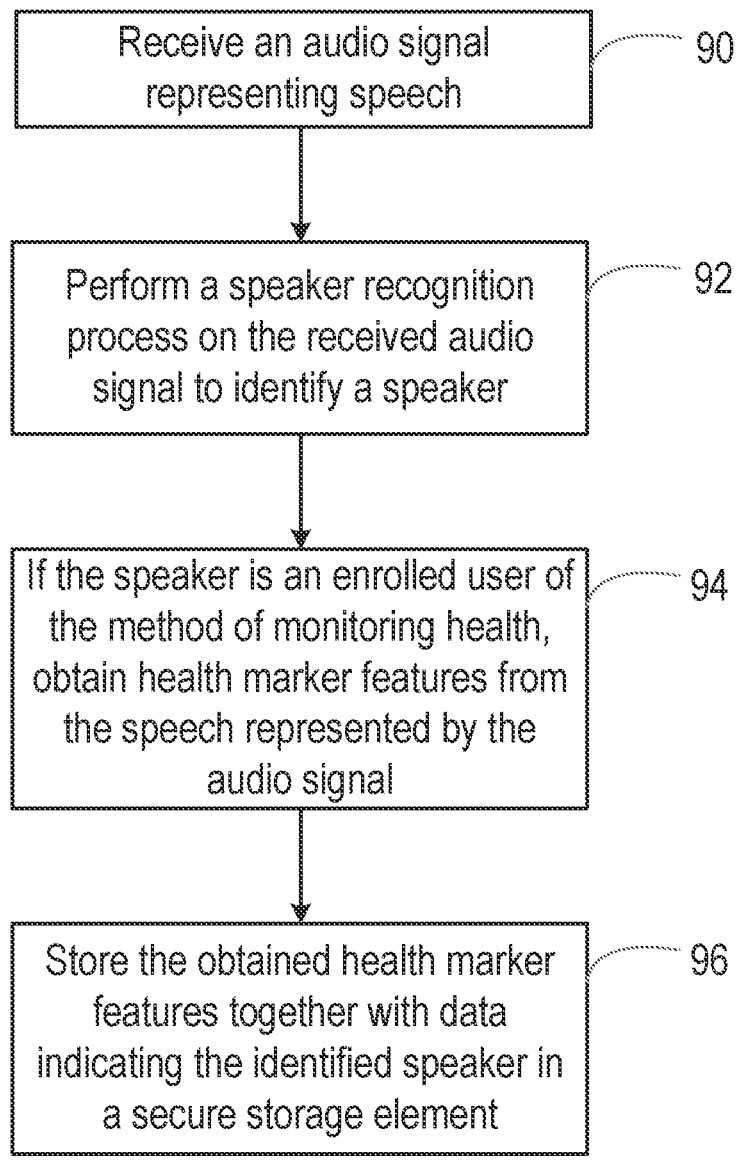
FIG. 6 is a flow chart, illustrating a second method.

FIG. 5 is a schematic block diagram of a system that can be implemented on the smartphone 10, and FIG. 6 is a flow chart illustrating a method performed by the system, for obtaining information that is relevant for use in monitoring a user's health.

FIG. 5 shows one of the microphones 12 on the smartphone 10. The microphone 10 will detect sounds in the vicinity of the smartphone 10. Although only one microphone 10 is shown in FIG. 5, the sounds detected by multiple microphones can be used in the method.

A signal generated by the microphone 10 is passed to a pre-processing block 70. For example, if the signal generated by the microphone 10 is an analog signal, the pre-processing block 70 may perform analog-to-digital conversion. The signal may also be divided into frames, for example of 20 ms duration, such that each frame can be considered separately.

The pre-processed signal is passed to a voice activity detection (VAD) block 72, which determines whether the detected sound comprises speech. Parts of the received audio signal that represent speech may be stored in a buffer for a fixed time period on a first-in, first-out basis. For example, the buffer may be able to store at least 5 seconds, or at least 10 seconds, of speech.

Thus, in step 90 of the process shown in FIG. 6, the system of FIG. 5 receives the audio signal representing the speech. The received audio signal will depend on the sounds that are detected by the microphone 12, which may include the speech of one or more people, plus associated background sounds.

The received audio signal representing speech is then passed to a feature extraction block 74.

The features that are extracted by the feature extraction block 74 include features representing the input audio that can be used for performing speaker recognition. For example, the features that are extracted could include Mel Frequency Cepstral Coefficients (MFCCs). Other features that can be extracted from the speech signal include Perceptual Linear Prediction (PLP) features, Linear Prediction (LPC) features, and bottleneck or tandem features extracted with a deep neural network (DNN). Acoustic features such as MFCCs, PLP features and LPC features can be combined with the DNN-extracted features.

In addition, the features that are extracted by the feature extraction block 74 include features representing the input audio that can be used for monitoring a speaker's health. Some features that can be used for monitoring a speaker's health are also features that can be used for performing speaker recognition, while other features that can be used for monitoring a speaker's health are different from features that can be used for performing speaker recognition. For example, the features that can be used for monitoring a speaker's health include the frequency components of the speech, the amplitude of the speech, and the pitch period, amongst other things.

Thus, in the flow chart of FIG. 6, in step 92, a speaker recognition process is performed on at least some or all of the features that are extracted by the feature extraction block 74 from the received audio signal. The speaker recognition process is performed in a speaker recognition block 76.

In one example described below, it is assumed that there is at least one registered user of the system, who has been through an enrolment process. The process of enrolment typically involves the user speaking some predetermined words or phrases, and extracted features of the user's speech then being used to form a model of the user's speech.

In this case, the process of enrolment may involve notifying the user that the enrolment is to enable a speaker recognition process that is to be used as part of a method for monitoring their health. In this way, the user's consent to this monitoring can be obtained.

The speaker recognition process performed in step 92 then involves the features extracted from the received audio signal being compared with the model. If a test for similarity is passed, it is determined that the received speech is that of the enrolled user.

If it is determined in step 92 that the speaker is an enrolled user of the method of monitoring health, the process passes to step 94, in which the features that are extracted by the feature extraction block 74 are passed to a health markers block 78, in which health marker features are obtained, based on the features that were extracted by the feature extraction block 74 from the speech represented by the audio signal. The features that are used for obtaining the health marker features may include some or all of the extracted features used for performing the speaker recognition process, and/or may include some extracted features that were not used for performing the speaker recognition process.

For example, the health marker features that are obtained could include one or more of: a fundamental frequency of the speech; the jitter, that is, a measure of the cycle-to-cycle variation in the fundamental frequency; the shimmer, that is, a measure of the cycle-to-cycle variation in the amplitude of the signal; a Long Term Average Spectrum of the speech; an articulation rate; a maximal phonation time (MPT); a Noise-to-Harmonic Ratio (NHR); a Harmonic-to-Noise Ratio (HNR); the Cepstral peak prominence (CPP); the Maximum Flow Declination Rate (MFDR); the glottal Contact Quotient or Closed Quotient (CQ), which is a measure of how much the glottis is closed during a Glottal Pulse Period (GPP); and a measure of the relative power (or amplitude) between first and second harmonic components (H1-H2). Research has identified medical conditions that are associated with all of these marker features.

For example, US2003/0078768 is entitled "Method for Analysis of Vocal Jitter for Near-Term Suicidal Risk Assessment", and there are many other published techniques for diagnosing medical conditions based on features of a person's speech. One problem with such techniques is the difficulty of obtaining samples of the person's speech in natural conditions, while being certain that the speech that is detected is in fact the speech of the person of interest.

In addition, the health markers block 78 may generate time stamp data to be associated with the health marker information, relating to a specific time at which the speech that gave rise to the health marker was produced. In addition, or alternatively, the health markers block 78 may generate data relating to a duration of the relevant speech. In addition, or alternatively, the health markers block 78 may record health marker values that apply to specific time intervals. As just one illustrative example, the health markers block 78 may record values of the jitter for periods Monday 09:00-12:00, Monday 12:00-15:00, etc, and may similarly record values of the shimmer for periods Monday 09:00-12:00, Monday 12:00-15:00, etc.

In step 96 of the process shown in FIG. 6, any obtained health markers are stored, together with data indicating the identified speaker. For example, as shown in FIG. 5, the data may be stored in a memory 80. As described in more detail below, the memory 80 may be a secure storage device, which may be integrated with the processor that performs the analysis and classification in a System on a Chip, or may be securely connected to the processor.

In some cases, the relevant parts of the received signal may be stored in their entirety, so that a clinician can hear the person's speech.

As described above, the health markers are obtained only if the speech is identified as that of the enrolled user. In other examples, to avoid any processing delay, the process of obtaining the health markers can be performed without waiting for a determination that the speech is that of the enrolled user. In that case, if health markers are obtained, but it is determined that the speech is not that of the enrolled user, the health markers can be discarded.

As a further alternative, to avoid performing unnecessary computations, the features that are used for obtaining health markers are extracted only when it has been determined that the speech is that of the enrolled user. To enable this, the speech may be buffered before the features are extracted, and the process of extracting the features that are to be used for obtaining the health markers may be started only when it has been determined that the speech is that of the enrolled user.

In any event, the health markers are stored only if it is determined that the speech from which they were derived was the speech of a user who has enrolled into the health monitoring system.

Thus, this method and system have the advantage that clinically relevant information about the user's speech can be stored. In particular, the method and system are able to distinguish the speech of the person using the device, who has enrolled into the method of monitoring health, so that the clinically relevant information that is stored relates only to that enrolled person.

As shown in the embodiment of FIGS. 3 and 4, and the embodiment of FIGS. 5 and 6, medically relevant information is generated and stored.

One aspect of this disclosure concerns the way in which access to that stored information is restricted. Having generated and stored the medically relevant information, there is an issue with how that information might be released to other relevant services. For example, the user might be happy for all of the data to be available to a medical practitioner that they have approved. However, it will not usually be efficient for such a medical practitioner to review the large quantity of data that might be generated. Rather, it may be more efficient for all of the data to be given an initial assessment, with a qualified medical practitioner being alerted only when the data raises a particular concern. That initial assessment might for example be performed automatically by a software program. In the case of a system that is running on a smartphone, the software program might be running on a separate processor in the smartphone, and the data that is made accessible to the program might then also be accessible to other programs, when the user might not want this to happen.

Figure 7:
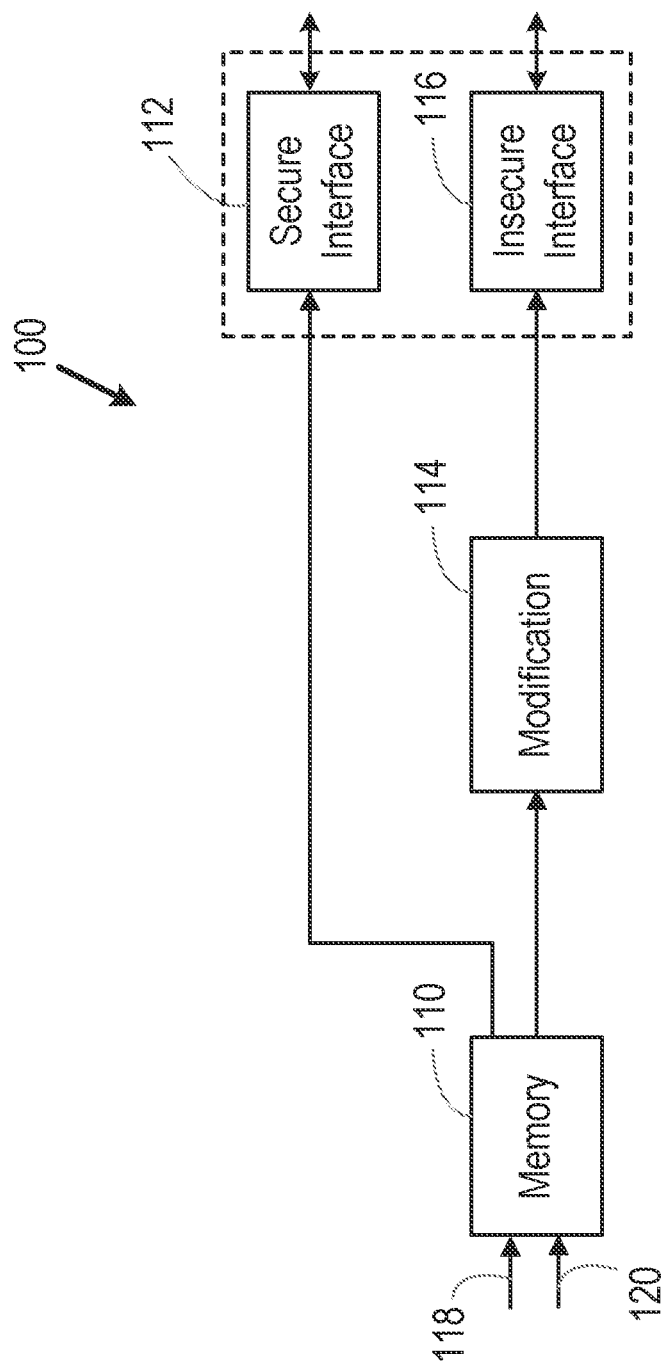
FIG. 7 is a block diagram, illustrating a third processing system.

FIG. 7 is a schematic block diagram, showing one form of a data storage system 100 for medically relevant information.

The system 100 comprises a memory 110, which is used to store medically relevant information that has been identified as relating to a particular person. When used in conjunction with a system as shown in FIG. 3, the memory 110 may be the same as the memory 38 shown in FIG. 3. Thus, in the case of information derived from a person's speech, a voice biometric process may have been performed on the speech. When used in conjunction with a system as shown in FIG. 5, the memory 110 may be the same as the memory 80 shown in FIG. 5. Thus, in the case of information derived from non-speech sounds, either a biometric process may have been performed on the sounds, or some other confirmation of identity may have been received.

Thus, the input 118 to the memory 100 may come from a system that provides identity information. In addition, the memory 100 may also have an input 120 for receiving input data from a separate device, for example such as a heart rate monitor or an activity monitor, that can provide medically relevant information.

Data that is stored in the memory 110 can be read through a secure interface 112. For example, the secure interface 112 may connect to an authenticated, or cryptographically secured link (for example using a Secure Sockets Layer (SSL), with public/private key encryption) such that only an authorised user can interrogate the stored data and/or such that the stored data can be sent only to an authorised user. The authorised user may for example be a clinician authorised by the owner of the smartphone.

In addition, the data that is stored in the memory 110 can be passed to a modification block 114, and then read through an insecure interface 116. The modifications performed by the modification block 114, and the operation of the insecure interface 116, are such that the data is obfuscated. For example, in some embodiments, the technique of differential privacy is applied.

For example, the data modification block 114 may be configured for subsampling all or a subset of the data received from the memory 110. This has the effect that the data that can be accessed through the insecure interface 116 is obfuscated, for example statistically obfuscated, and it is not possible to access the entirety of the data.

As another example, the data modification block 114 may be configured for adding noise to the data received from the memory 110.

As still another example, the data modification block 114 may be configured for generated aggregated statistics concerning the data received from the memory 110.

In conjunction with some or all of these techniques, the insecure interface 116 is configured such that only a predetermined maximum number of accesses are permitted to the data generated by the data modification block 114. This may permit only a predetermined maximum number of total accesses, or may permit only a predetermined maximum number of accesses in a given time period. The purpose of the data modification block is to modify the data so that it is not possible to obtain accurate information that can be associated with a specific person. However, if the number of permitted data accesses were unlimited, a hostile actor could deduce that accurate information by combining the partial or noisy data obtained from those repeated accesses. Similarly, the number of transmissions of the data generated by the data modification block 114 may also be restricted.

Output data may be provided to a health decision engine, which performs an initial automated analysis of the data. In appropriate circumstances, the health decision engine may generate an output direct to the user (for example "seek urgent medical advice", "arrange a routine medical consultation", "review your medication", "no cause for concern", etc). In other circumstances, the health decision engine may decide that the data should be transmitted for full review and analysis by a clinician. Thus, if the health decision engine is relatively insecure, it may have partial access to the stored data in a form that does not allow the identity of the user to be deduced and/or that does not allow detailed information about the health of the user to be obtained. However, the health decision engine may have sufficient information that it can prompt the user to seek more detailed advice in the event that the partial access to the data suggests that this would be desirable.

The health decision engine may be provided as a downloadable application on the smartphone 10, for example running on a separate processor to the processor that handles the original health-related information, or the health decision engine may be provided on a remote server, with the output data being transmitted from the device on a regular basis.

Figure 8:
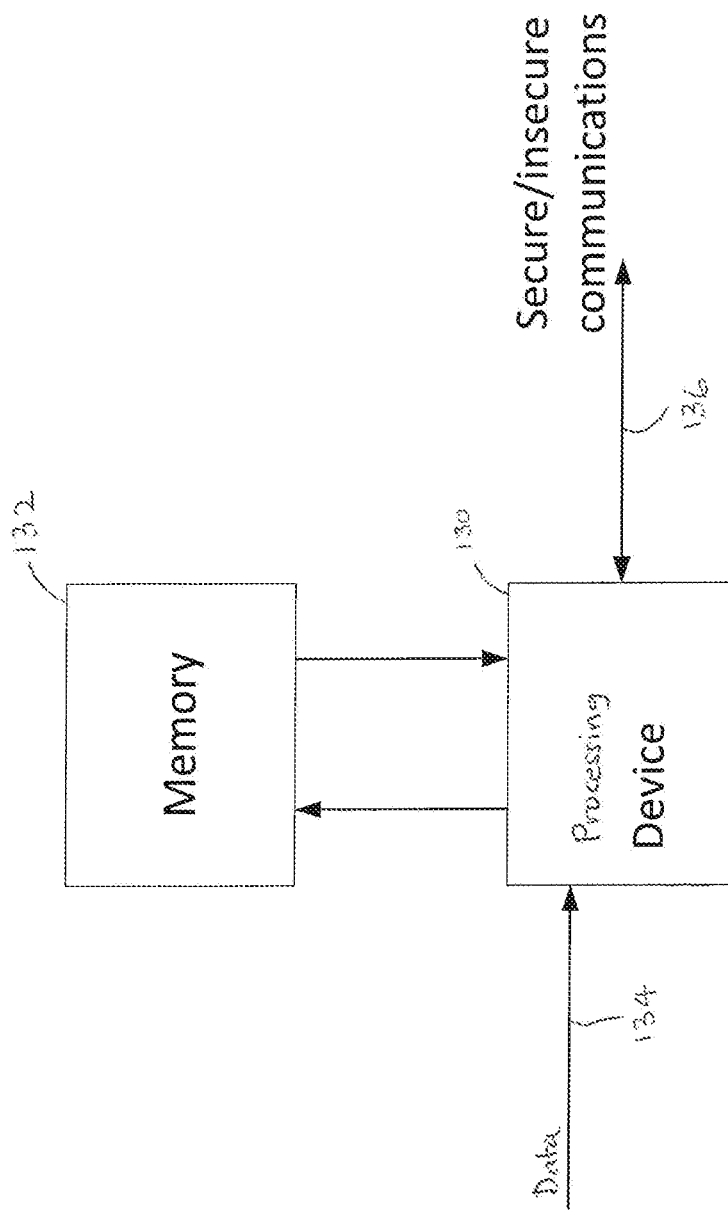
FIG. 8 is a block schematic diagram of a processing and storage device.

FIG. 8 is a schematic diagram, showing an alternative form of a health-related information generation and storage system, in accordance with aspects of the disclosure. Specifically, FIG. 8 shows a processing device 130, which may for example be in the form of a digital signal processor (DSP). The processing device is connected to a memory device 132.

An input 134 allows data to be supplied to the processing device 130, while an interface 136 allows data to be supplied from the processing device 130, in either a secure or an insecure manner.

In some embodiments, the processing device 130 and the memory device 132 are packaged as a single integrated circuit, with the memory for example being provided as non-volatile RAM.

In other embodiments, the memory device 132 may be provided as a separate chip from the processing device 130, in which case data may be encrypted before it is written from the processing device 130 to the memory device 132, in order to prevent interception of communications with the memory.

In some embodiments, the processing device 130 may be a single integrated circuit that receives a pre-processed audio signal, and performs all of the subsequent processing and analysis. For example, in the case of a system as shown in FIG. 3, the sound analysis block 32 and the biometric analysis block 34 may both be implemented in the processing device 130. Similarly, in the case of a system as shown in FIG. 5, the feature extraction block 74, the speaker recognition block 76, and the health markers block 78 may all be implemented in the processing device 130.

In other embodiments, the processing device 130 may receive extracted features of the audio signal. For example, in the case of a system as shown in FIG. 3, the feature extraction may be performed on a separate device, while the analysis elements of the sound analysis block 32 and the biometric analysis block 34 are implemented in the processing device 130. Similarly, in the case of a system as shown in FIG. 5, the feature extraction block 74 may be implemented in a separate device, while the speaker recognition block 76 and the health markers block 78 may be implemented in the processing device 130.

In still other embodiments, the processing device 130 manages the storage of data received from separate blocks, and controls the access thereto. For example, in the case of a system as shown in FIG. 3, the processing device 130 may receive output data from the sound analysis block 32 and the biometric analysis block 34. Similarly, in the case of a system as shown in FIG. 5, the processing device 130 may receive output data from the feature extraction block 74, the speaker recognition block 76, and the health markers block 78.

In all of these embodiments, the processing device 130 may control the access to data stored in the memory device 132.

Thus, for example, the processing device 130 may control both secure and insecure access to the stored data. The secure and insecure interfaces may be provided on separate communications lines or on the same communications line.

As described in more detail above with reference to FIG. 7, the processing device may ensure that full access to the stored data is only available to an authorised user over a cryptographically protected link. Access to the stored data over the insecure interface is permitted only in ways that protect the privacy of the user. For example, only partial access to the data may be allowed, such that the privacy of the user is not compromised by that partial data. For example, the data may be accessed in such a way that the identity of the user is not released, and also that the amount of data that is released is not sufficient to allow the identity of the user to be deduced.

Thus, the system is able to obtain and store health-related information in a way that allows detailed information about a user's condition to be obtained, but that restricts access to that information to protect the privacy of the user to an acceptable degree.

The skilled person will recognise that some aspects of the above-described apparatus and methods may be embodied as processor control code, for example on a non-volatile carrier medium such as a disk, CD- or DVD-ROM, programmed memory such as read only memory (Firmware), or on a data carrier such as an optical or electrical signal carrier. For many applications embodiments of the invention will be implemented on a DSP (Digital Signal Processor), ASIC (Application Specific Integrated Circuit) or FPGA (Field Programmable Gate Array). Thus the code may comprise conventional program code or microcode or, for example code for setting up or controlling an ASIC or FPGA. The code may also comprise code for dynamically configuring re-configurable apparatus such as re-programmable logic gate arrays. Similarly the code may comprise code for a hardware description language such as Verilog™ or VHDL (Very high speed integrated circuit Hardware Description Language). As the skilled person will appreciate, the code may be distributed between a plurality of coupled components in communication with one another. Where appropriate, the embodiments may also be implemented using code running on a field-(re)programmable analogue array or similar device in order to configure analogue hardware.

Note that as used herein the term module shall be used to refer to a functional unit or block which may be implemented at least partly by dedicated hardware components such as custom defined circuitry and/or at least partly be implemented by one or more software processors or appropriate code running on a suitable general purpose processor or the like. A module may itself comprise other modules or functional units. A module may be provided by multiple components or sub-modules which need not be co-located and could be provided on different integrated circuits and/or running on different processors.

Embodiments may be implemented in a host device, especially a portable and/or battery powered host device such as a mobile computing device for example a laptop or tablet computer, a games console, a remote control device, a home automation controller or a domestic appliance including a domestic temperature or lighting control system, a toy, a machine such as a robot, an audio player, a video player, or a mobile telephone for example a smartphone.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope.

The invention claimed is:

1. A method of monitoring an enrolled user's health, comprising:
   receiving an audio signal representing speech;
   performing a speaker recognition process on the received audio signal to identify a speaker;
   if it is determined that the identified speaker is an enrolled user, obtaining health marker features from the speech represented by the audio signal; and
   storing the obtained health marker features together with data indicating the identified speaker in a secure storage element.

2. A method according to claim 1, comprising extracting features of the received audio signal, and obtaining said health marker features from the extracted features.

3. A method according to claim 2, comprising performing said speaker recognition process using the same extracted features as are used to obtain said health markers.

4. A method according to claim 1, comprising applying a time stamp to each health marker feature, and storing the time stamp with the health marker feature in the secure storage element.

5. A method according to claim 1, comprising obtaining the health marker features over at least one time period, and storing data identifying the time period with the health marker feature in the secure storage element.

6. A method according to claim 1, wherein the health marker features comprise one or more of: a fundamental frequency of the speech; Jitter; Shimmer; a Long Term Average Spectrum of the speech; an articulation rate; a maximal phonation time; a Noise-to-Harmonic Ratio (NHR); a Harmonic-to-Noise Ratio (HNR); and a Cepstral peak prominence.

7. A system comprising:
   an input for receiving an audio signal representing speech; and
   a processor, for performing a speaker recognition process on the received audio signal to identify a speaker; if it is determined that the identified speaker is an enrolled user, obtaining health marker features from the speech represented by the audio signal; and storing the obtained health marker features together with data indicating the identified speaker in a secure storage element.

8. A device comprising a system according to claim 7, wherein the device comprises: a mobile computing device, a games console, a remote control device, a home automation controller or a domestic appliance, a toy, a machine, an audio player, a video player, or a mobile telephone.

9. A computer program product, comprising computer-readable code for causing a programmed processor to perform the method of claim 1.

10. A computer program product according to claim 9, comprising a tangible computer-readable medium for storing said code.

* * * * *